(12) United States Patent
Ducke

(10) Patent No.: US 10,583,023 B2
(45) Date of Patent: Mar. 10, 2020

(54) ENDOGRAFT INTRODUCER ASSEMBLY HAVING A TRANSFER SHEATH

(71) Applicant: COOK MEDICAL TECHNOLOGIES LLC, Bloomington, IN (US)

(72) Inventor: Werner D. Ducke, Queensland (AU)

(73) Assignee: Cook Medical Technologies LLC, Bloomington, IN (US)

( * ) Notice: Subject to any disclaimer, the term of this patent is extended or adjusted under 35 U.S.C. 154(b) by 748 days.

(21) Appl. No.: 15/074,084

(22) Filed: Mar. 18, 2016

(65) Prior Publication Data

US 2016/0270937 A1 Sep. 22, 2016

(30) Foreign Application Priority Data

Mar. 18, 2015 (AU) ................................ 2015201411

(51) Int. Cl.
*A61F 2/966* (2013.01)
*A61F 2/97* (2013.01)

(52) U.S. Cl.
CPC ............... *A61F 2/966* (2013.01); *A61F 2/97* (2013.01); *A61F 2250/0071* (2013.01)

(58) Field of Classification Search
CPC .... A61F 2250/0071; A61F 2/966; A61F 2/97; A61B 2017/0414; A61B 2017/0441; A61B 17/0401
See application file for complete search history.

(56) References Cited

U.S. PATENT DOCUMENTS

| 6,228,073 B1 * | 5/2001 | Noone ............... A61M 25/0014 128/912 |
| 6,254,628 B1 * | 7/2001 | Wallace ........... A61B 17/12118 606/108 |
| 7,163,552 B2 | 1/2007 | Diaz |

(Continued)

FOREIGN PATENT DOCUMENTS

| EP | 2749258 A1 | 7/2014 |
| WO | WO 2014/204758 A1 | 12/2014 |

OTHER PUBLICATIONS

European Search Report for corresponding EP Application No. 16275001.2 dated Jul. 13, 2016, 8 pages.

(Continued)

*Primary Examiner* — Shaun L David
*Assistant Examiner* — Christina C Lauer
(74) *Attorney, Agent, or Firm* — Brinks Gilson & Lione

(57) ABSTRACT

An endograft introducer assembly having a transfer sheath is disclosed. The assembly includes a pusher assembly comprising a guide wire catheter, a tip mounted to a proximal end of the guide wire catheter, a stent graft receiving portion distal of the tip and a pusher distal of the receiving portion. The assembly further includes a transfer sheath extending distally over the stent graft receiving portion from a proximal position adjacent to the tip, the transfer sheath having a first length over the stent graft receiving portion; and a stopper disposed co-axially around the transfer sheath. The stopper has a proximal end terminating in a stopper surface and a distal portion, the distal portion removably engaged with the transfer sheath so as to prevent relative axial movement between the stopper and the transfer sheath in at least one direction.

19 Claims, 6 Drawing Sheets

(56) References Cited

U.S. PATENT DOCUMENTS

| | | |
|---|---|---|
| 7,691,109 B2 | 4/2010 | Amstrong et al. |
| 8,506,623 B2 | 8/2013 | Wilson et al. |
| 8,597,277 B2 | 12/2013 | Lenker et al. |
| 2007/0156084 A1* | 7/2007 | Belhe ............... A61B 17/00491 604/57 |
| 2008/0264102 A1 | 10/2008 | Berra |
| 2009/0204197 A1 | 8/2009 | Dorn et al. |
| 2012/0296313 A1 | 11/2012 | Andreacchi et al. |
| 2012/0296407 A1 | 11/2012 | Caselnova |
| 2014/0188211 A1* | 7/2014 | Roeder .................. A61F 2/966 623/1.12 |
| 2014/0379065 A1* | 12/2014 | Johnson .................. A61F 2/958 623/1.11 |

OTHER PUBLICATIONS

Australian Patent Examination Report No. 1 for corresponding AU 2015201411, dated Apr. 10, 2015, 5 pages.

\* cited by examiner

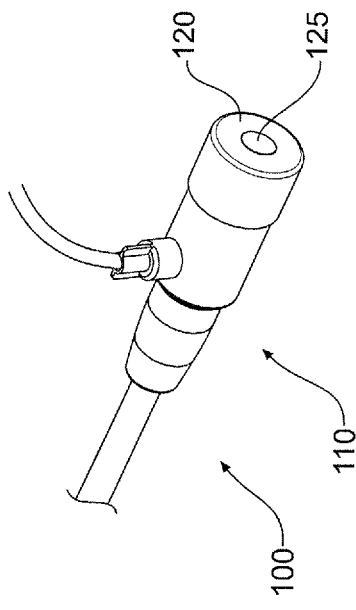
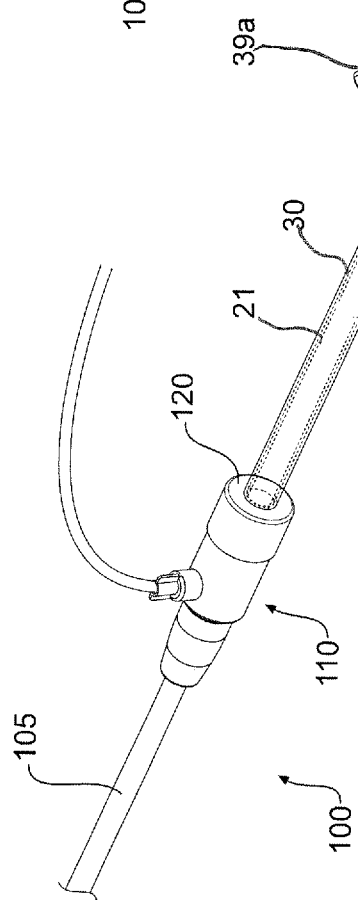
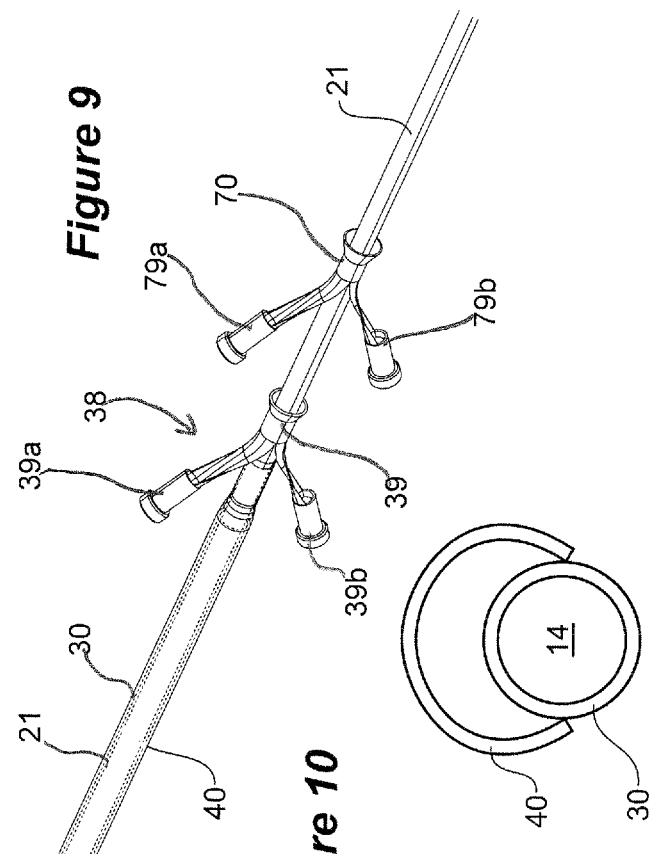

ENDOGRAFT INTRODUCER ASSEMBLY HAVING A TRANSFER SHEATH

RELATED APPLICATIONS

The present patent document claims the benefit of priority to Australian Patent Application No. 2015201411, filed Mar. 18, 2015, and entitled "An Endograft Introducer Assembly Having A Transfer Sheath," the entire contents of each of which are incorporated herein by reference.

TECHNICAL FIELD

The invention relates to medical devices and more particularly to a medical device used for deployment of an intraluminal graft or stent graft, otherwise referred to as an introducer or a stent graft introducer. In particular, this invention relates to an endograft introducer assembly having a transfer sheath to deliver the stent graft into a main sheath of an introducer assembly.

BACKGROUND

In the deployment of a graft, or stent graft, into the human or animal body via intraluminal techniques, a deployment device is used to introduce the stent graft into a lumen of the body and, after the stent graft has been deployed and expanded within the lumen, the introducer assembly is retracted.

In some procedures, including some procedures using custom made devices, a main sheath assembly is required to be deployed into the vasculature independently of the graft. In such procedures, after the main sheath assembly is in place, a graft which is pre-compressed into a temporary tube or transfer tube is transferred into the main sheath of the main sheath assembly. At this time it is important that the transfer takes place safely smoothly. When using currently known endograft introducer assemblies, this results in an additional workload for operating room staff and can add risk to the procedure.

Brief Summary

BRIEF DESCRIPTION OF THE DRAWINGS

Embodiments of the present invention will be discussed with reference to the accompanying drawings wherein:

FIG. 9 is a close up view of a portion of the main sheath assembly shown in FIG. 8; and FIG. 10 is a similar view to that of FIG. 8 but is a close up view and shows the stopper of the introducer assembly abutting the main sheath assembly;

FIG. 11A shows a diagrammatic end view of a stopper of the introducer assembly of FIGS. 1 to 3 in an installed condition and being removed respectively.

FIG. 11B is a similar view to that of FIG. 11A, but shows the stopper being removed.

DETAILED DESCRIPTION OF THE DRAWINGS AND THE PRESENTLY PREFERRED EMBODIMENTS

Throughout this specification, the term "distal" with respect to a deployment device or an endograft means the end deployment device that is closest to the operator of the deployment device and the end of the endograft closest to the operator end of the deployment device, and the term "proximal" means the portion the deployment device or end of the endograft nearer the deployment end of the deployment device. When applied to other vessels, similar terms such as caudal and cranial should be understood.

Described and shown here is an endograft introducer assembly that includes a pusher assembly having a guide wire catheter, a tip mounted to a proximal end of the guide wire catheter, a stent graft receiving portion distal of the tip and a pusher distal of the receiving portion. A transfer sheath extends distally over the stent graft receiving portion from a proximal position adjacent to the tip and has a first length over the stent graft receiving portion. A stopper is disposed co-axially around the transfer sheath, and has a proximal end terminating in a stopper surface and a distal portion. The distal portion is removably engaged with the transfer sheath so as to prevent relative axial movement between the stopper and the transfer sheath in at least one direction. The stopper has a second length that may be less than the first length. The transfer sheath includes a return portion at its distal end which receives the distal end of the stopper to prevent relative axial movement between the stopper and the transfer sheath in the at least one direction. The assembly may be used to transfer a stent graft to a main sheath.

The distal end of the transfer sheath may include a bifurcated end that has grippable tails that may be pulled to remove the transfer sheath in a peelaway fashion. The return portion of the transfer sheath is that part of the transfer sheath that folds back on itself and includes the gripable tails.

A distal portion of the stopper includes a transfer sheath receiving portion that has a receiving outer diameter and wherein the stopper surface has a stopper outer diameter with the stopper outer diameter larger than the receiving outer diameter. The stopper may have a longitudinal split that allows the stopper to flexibly open for lateral movement over the transfer sheath.

The stopper has a first longitudinal stiffness and the transfer sheath has a second longitudinal stiffness, the first longitudinal stiffness may be greater than the second longitudinal stiffness. The transfer sheath is frangible so as to allow it to be removed from the pusher without the need to slide over an end of the pusher. The assists in the peelaway capability of the transfer sheath.

Figure 1:
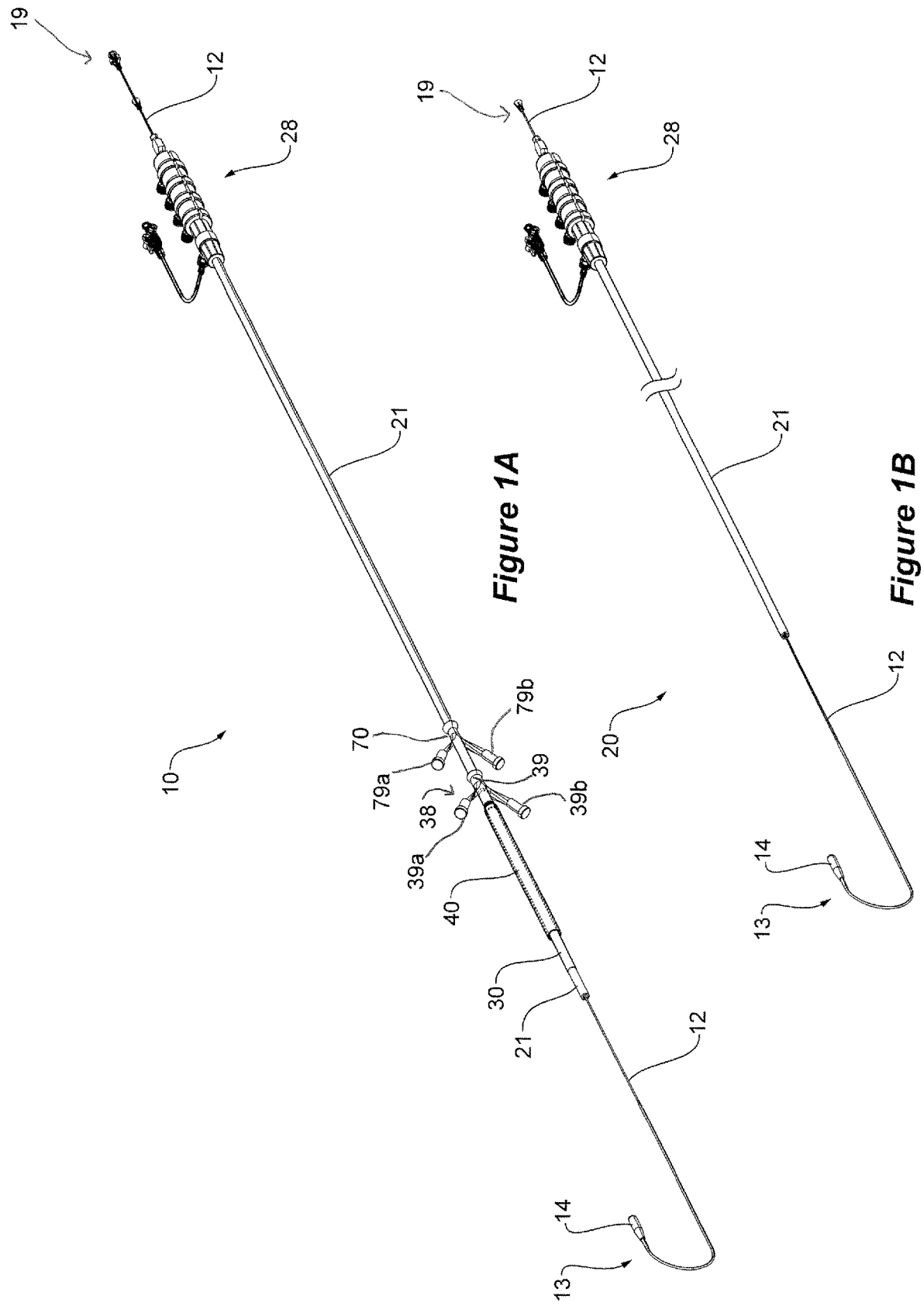
FIG. 1A is a perspective view of an endograft introducer assembly according to the invention.
FIG. 1B is a perspective view of a pusher assembly which forms part of the endograft introducer assembly of FIG. 1A.

FIG. 1A is a perspective view of an endograft introducer assembly 10. FIG. 1B shows a pusher assembly 20 of the endograft introducer assembly 10. The endograft introducer assembly 10 includes a pusher assembly 20, as shown in 1B. The pusher assembly 20 includes a guide wire catheter 12, a tip 14 mounted to a proximal end 13 of the guide wire catheter 12, a pusher 21, and a handle 28 at the distal end 19. The guide wire catheter 12 extends from the distal end 19 to the tip 14 as shown in FIG. 1A. As further shown in FIG. 1A, the endograft assembly 10 further includes a transfer sheath 30 disposed at least partially over the pusher 21, and stopper 40 disposed at least partially over the transfer sheath 30.

Figure 2:
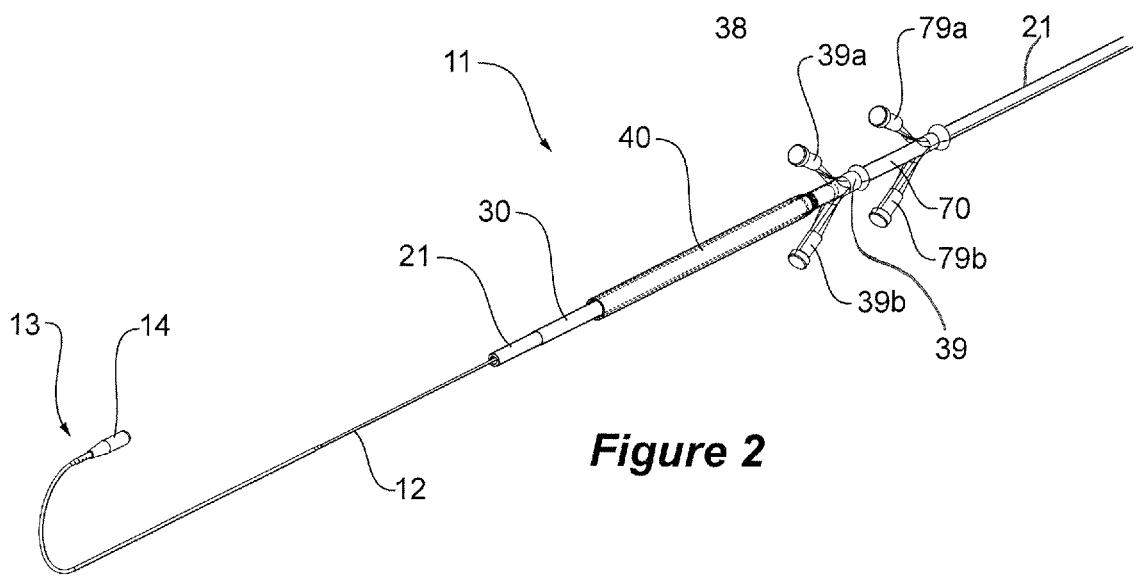
FIG. 2 is a close up view of a proximal end of the introducer assembly of FIG. 1A.
Figure 3:
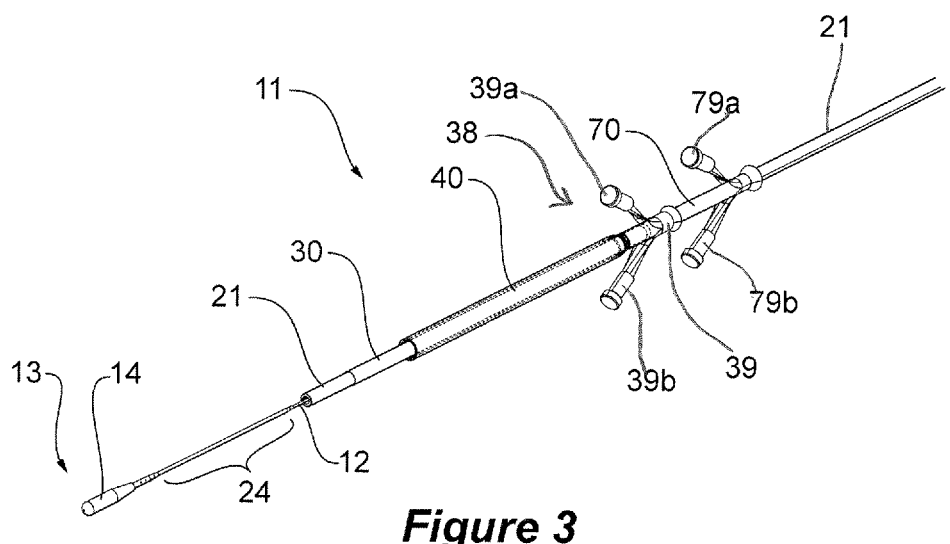
FIG. 3 is a similar view to that of FIG. 2, but shows a guide wire catheter and tip, also shown in FIGS. 1 and 2, in a straightened condition.
Figure 4:
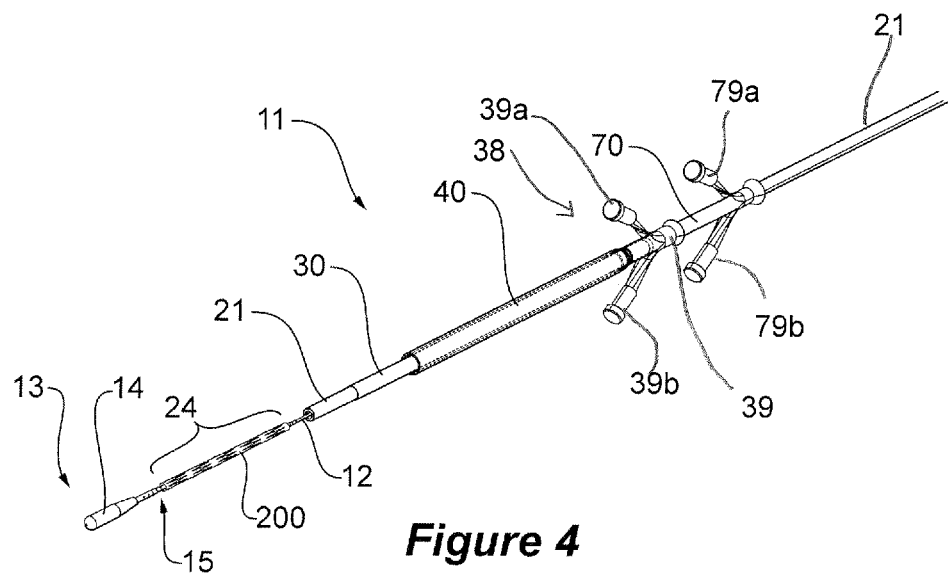
FIG. 4 is a similar view to that of FIG. 3, but shows the introducer assembly of FIGS. 1 to 3 loaded with a stent graft.
Figure 5:
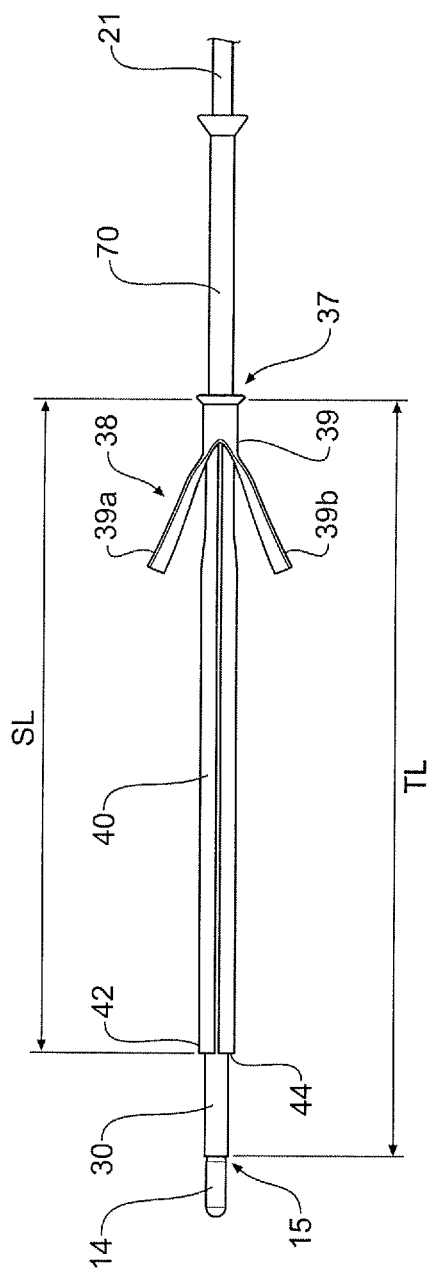
FIGS. 5 and 6 are diagrammatic views showing a portion of the introducer assembly shown in FIG. 4, but with the stent graft retracted and covered by a transfer sheath.
Figure 6:
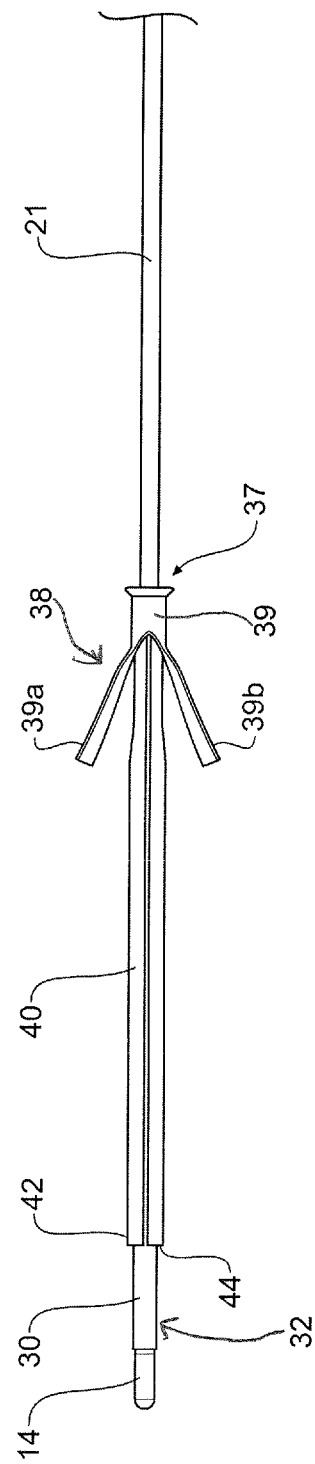

Referring now to FIGS. 2-4. FIGS. 2-4 are perspective views of the proximal end portion 11 of the endograft introducer assembly 10 of FIG. 1. As shown in FIG. 2, the proximal end portion 11 includes the guide wire catheter 12, a tip 14 at the proximal end 13 of the guide wire catheter 12, the pusher 21 at least partially disposed over the guide wire catheter 12, the transfer sheath 30 disposed at least partially over the pusher 21, and the stopper 40 disposed at least partially over the transfer sheath 30. As such, at one point along the length of the proximal end portion 11, the guide wire catheter 12, the pusher, 21, the transfer sheath 30, and the stopper 40 are concentrically arranged. As further shown in FIG. 1A, the transfer sheath 30 includes a return portion 39 that extend back over the transfer sheath in a bifurcated end 38 terminating in a pair of gripable tails 39a and 39b, which also extend back over the transfer sheath as shown in FIGS. 5 and 6, and which tails allow the operator to peel and remove the transfer sheath 30 from the pusher assembly 20, by pulling on the tails 39a and 39b to peel them away and remove the transfer sheath. Further shown is a peelaway plug 70 also having grippable tails 79a and 79b, all of which are explained in further detail below. The proximal end portion 11 of the endograft introducer assembly 10 is shown in greater detail FIG. 2. FIG. 2 shows many of the same components as FIGS. 1A and 1B. FIG. 3 includes the same components as shown in FIG. 2, a stent graft receiving region 24 and that the pusher 21 is distal of the stent graft receiving region 24. FIG. 4 includes the same components as shown in FIGS. 2 and 3, but further shows a stent graft 200 mounted on the stent graft receiving region 24.

FIGS. 5 and 6 are diagrammatic views showing a portion of the introducer assembly shown in FIG. 4, but with the stent graft retracted and covered by a transfer sheath. FIGS. 5 and 6 shows the tip 14 of the guide wire catheter 12 (not shown here), the transfer sheath, the stopper 40, the bifurcated end 38 with its grippable tails 39a, 39b, the peelaway plug 70, and the pusher 21. As shown, the stopper 40 is coaxially around the transfer sheath 30. FIGS. 5-6 further show that the stopper proximal end 42 terminates in a stopper surface 44 (shown more clearly in FIG. 7A). As shown in FIG. 5, the stopper 40 has a longitudinal split 45, which purpose is described in further detail below. As shown, the transfer sheath 30 has a first length TL, which length is sufficient to entirely cover the stent graft 200 illustrated in FIG. 4. The stopper 40 has a second length SL, which is less than the first length TL. This is explained further below when use of the introducer assembly 10 is explained.

As shown in FIG. 5, the transfer sheath 30 is in a position extending distally over the stent graft 200 (not shown in FIG. 5) from a proximal position 15 adjacent to the tip 14. As set forth above, a stopper 40 is disposed coaxially around the transfer sheath 30 and the stopper 40 has a proximal end 42 terminating in a stopper surface 44.

Figure 7A:
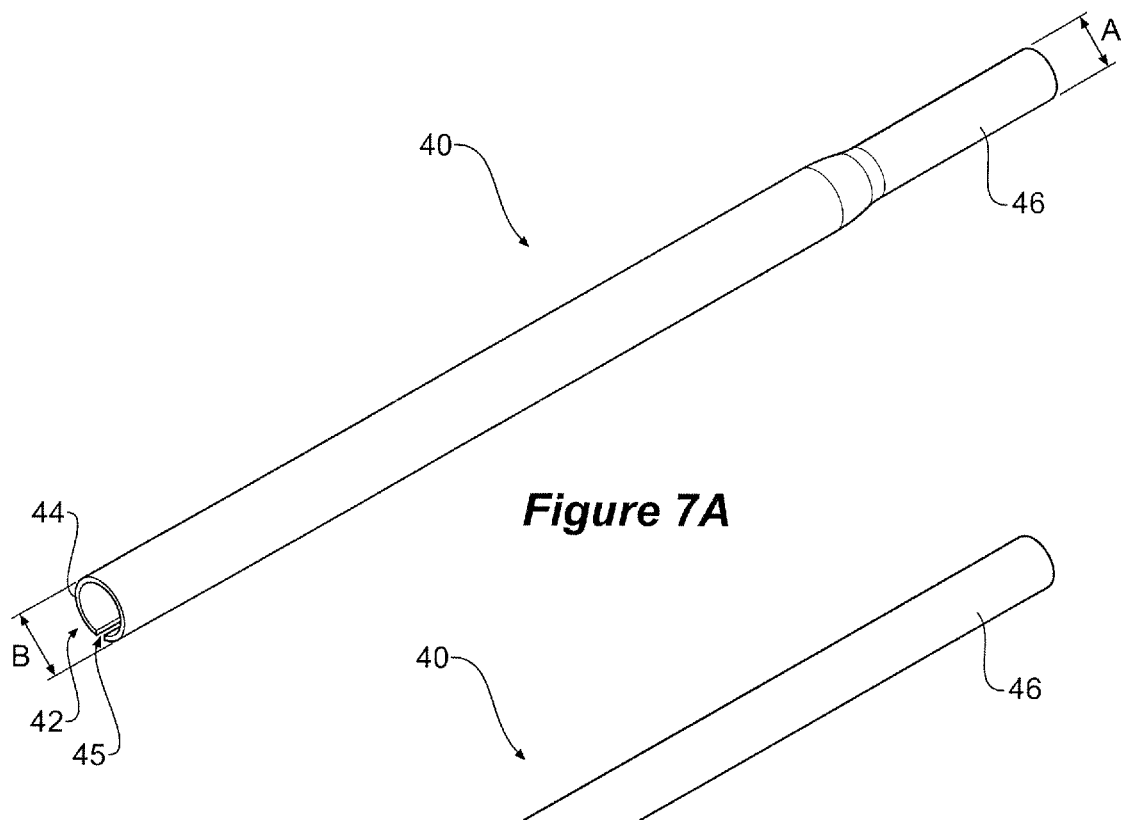
FIG. 7A is a detailed perspective view of a stopper, the stopper being a component of the introducer assembly shown in FIGS. 1 to 6.

This stopper surface 44 is more clearly shown in FIG. 7A. FIG. 7A shows that the stopper 40 has a distal portion 46. The distal portion 46 is removably engaged with the transfer sheath 30 so as to prevent relative movement between the stopper 40 and the transfer sheath 30 in at least one direction. More specifically, when the stopper surface 44 of the stopper 40 is pushed against a surface, such as the distal end face 120 of the valve assembly 110 shown in FIGS. 9 and 10, the reaction force is transferred along the a stopper 40 to its distal portion 46 thereby preventing movement of the transfer sheath 30 towards the distal end face 120 (which functions as a reaction surface) as the pusher 21 is pushed in a direction towards the distal end face 120.

Figure 7B:
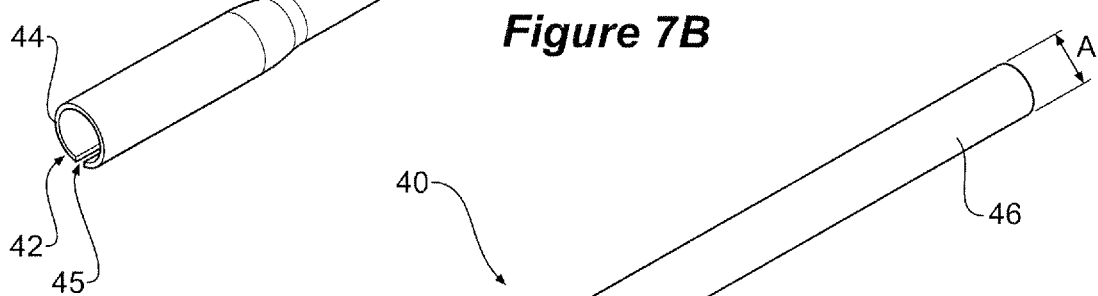
FIGS. 7B and 7C show alternative embodiments of the stopper shown in FIG. 7A.
Figure 7C:
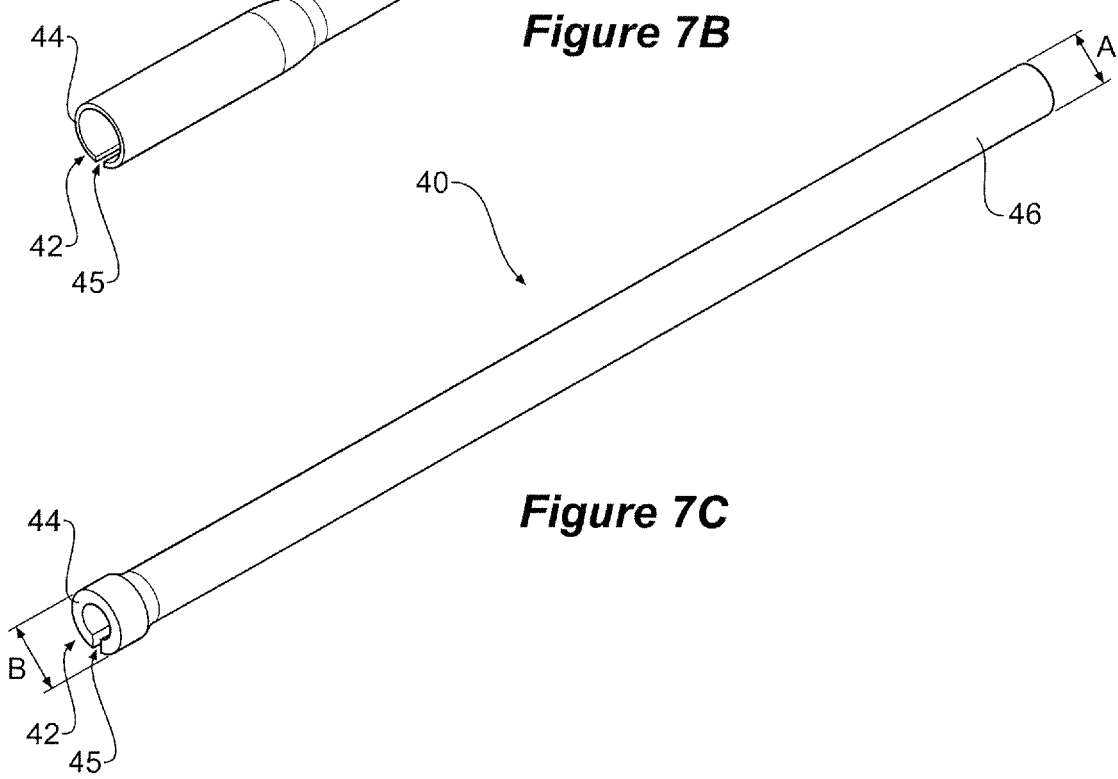

The stopper 40, as shown in FIGS. 5, 6, 7A and FIG. 11A, has a longitudinal split 45. The split 45 allows the stopper 40 to flexibly open for lateral movement over the transfer sheath 30. FIG. 11B shows the stopper forced open for removal from around the transfer sheath 30. In other embodiments of the invention, alternative stoppers can be used. For instance, the stopper 40 illustrated in FIG. 7B or the stopper 40 illustrated in FIG. 7C can be used.

Referring again to FIG. 7A, the distal portion 46 of the stopper 40 has a receiving outer diameter A. This receiving outer diameter A receives the return portion 39 of the transfer sheath 30, as is shown in FIGS. 5 and 10. The return portion 39 is configured and constructed to prevent relative axial movement between the stopper 40 and the transfer sheath 30 in one direction. As shown in FIG. 10, transfer sheath 30 has a bifurcated end 38 with the gripable portions 39a and 39b. The first dotted line within the stopper 40 is the guide wire catheter 21 and the second dotted line over the first dotted line is the transfer sheath 30. The transfer sheath 30 ends with its bifurcated end 38 where the gripable portions 39a and 39b return over the transfer sheath 30 to form the return portion 39 within which the distal portion 46 of stopper 40 is received. In other words, although the stopper 40 is coaxial over the transfer sheath 30, at the distal end 37 of the transfer sheath, the return portion extends over the distal end of the stopper 40 to form the return portion 39 in into which the stopper distal portion 46 extends. Hence, as set forth herein, as the components move toward the valve and the surface 44 of the stopper 40 abuts the surface 120 of the valve, the transfer sheath 30 can only move into the valve housing for the distance that is the difference between TL and SL because the receipt of the end 46 of the stopper 40 in the return portion 39 of the transfer sheath 30 prevents further movement in that direction.

The receiving outer diameter A is smaller than the stopper surface 44 outer diameter B, as indicated on FIG. 7A. This allows the stopper 40 to snuggly fit around the transfer sheath 30 at its distal end 37. Also, where the stopper 40 has a constant wall thickness, such as in the embodiment shown in FIG. 7A (and FIG. 7B), the stopper loosely fits around the transfer sheath 30 at, or towards, its proximal end 32.

The transfer sheath 30 is frangible so as to allow it to be removed from the pusher 21 without the need to be slid over an end of the pusher 21. As set forth above, the transfer sheath 30 comprises a bifurcated end 38 terminating in a pair of gripable tails 39a and 39b as shown in FIG. 2. These gripable tails 39a and 39b allow the operator to peel and remove the transfer sheath 30 from the pusher assembly 20. The transfer sheath 30 can thus be considered a "peelaway" component.

As set forth above, FIGS. 1-4 and 8 and 10 show a peelaway plug 70. This peelaway plug 70 is provided to plug the distal end 37 of the transfer sheath 30. This ensures that the introducer assembly 10 can be flushed with a flushing fluid. The peelaway plug 70 may include gripable tails 78a and 78b, as illustrated. Alternative plugs, such as the plug 70 schematically illustrated in FIG. 5, may be used Referring to FIG. 8, the introducer assembly 10 is shown over a guide wire 8 adjacent a main sheath assembly 100. FIG. 9 shows that the main sheath assembly 100 has a valve assembly 110 that has a distal end face 120 surrounding an aperture 125. Within the aperture 125 is a valve as is known in the art. The valve may be hemostatic and prevents, or at least minimizes, blood leakage. FIG. 10 shows the stopper 40 with its stopper surface 44 (shown in FIG. 8) abutting the distal end face 120 of the valve assembly 110. As mentioned above, the diameter B is larger than the diameter A, so as to ensure that the stopper surface 44 does not enter the aperture 125, and instead firmly abuts the annular distal end face 120, as is shown in FIG. 10.

Figure 8:
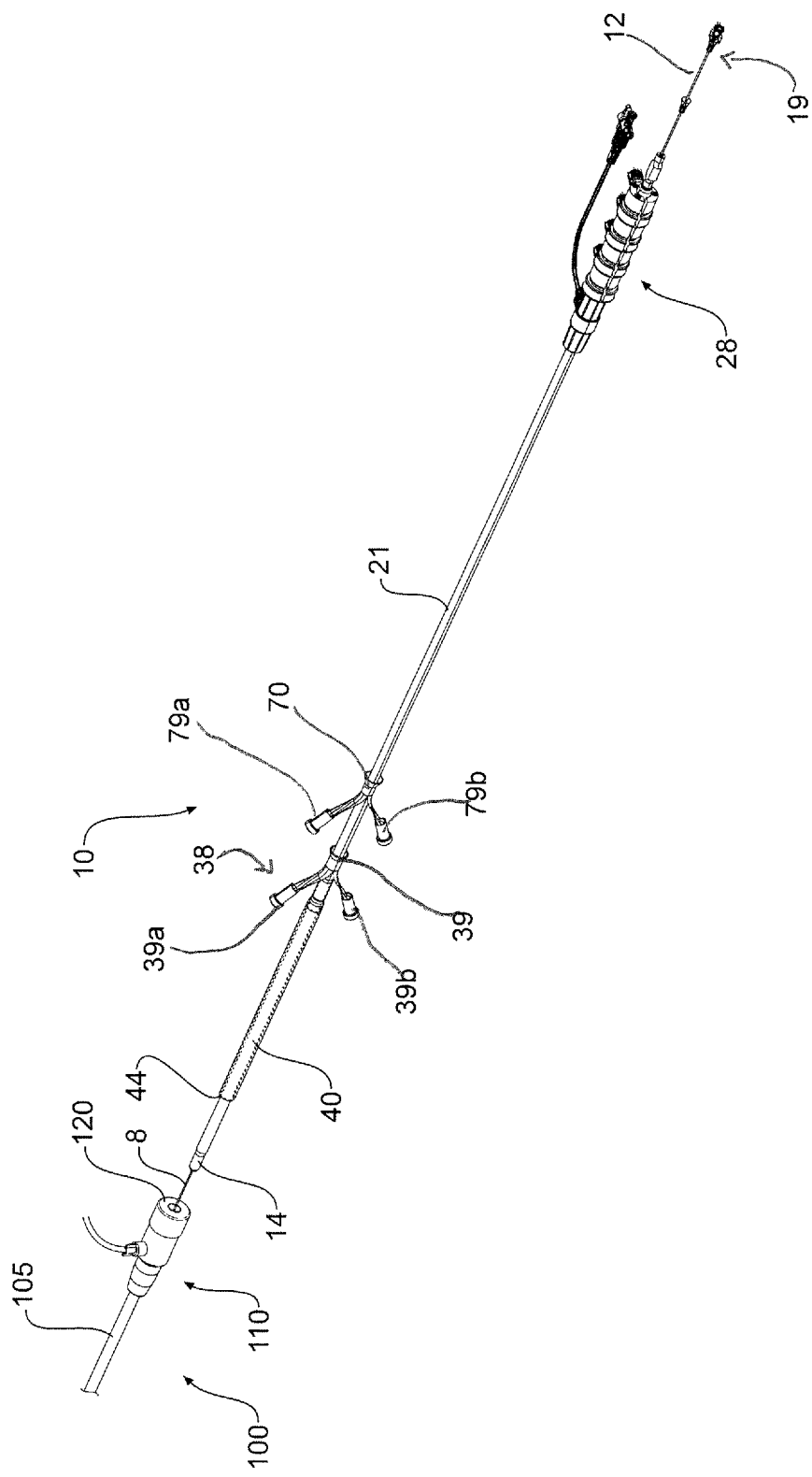
FIG. 8 shows a perspective view of the introducer assembly of FIGS. 1 to 6 on a guide wire being guided towards a main sheath assembly.

The stopper 40 has a first longitudinal stiffness and the transfer sheath 30 has a second longitudinal stiffness. The first longitudinal stiffness is greater than the second longitudinal stiffness. The longitudinal stiffness of the stopper 40 is such that when a person pushes the pusher 21 axially along the guide wire 8, as shown in FIG. 8 in the direction of the arrow, towards the main sheath assembly 100 so that the stopper surface 44 abuts the distal end face 120, a reaction force is transmitted from the stopper surface 44 along the stopper 40 to the proximal end 32 of the transfer sheath 30. This reaction force is sufficient to prevent further movement of the transfer sheath 30 and thereby only allows the transfer sheath 30 to travel a small distance into the main sheath assembly 100. This distance is the difference between the lengths TL and SL, as illustrated in FIG. 5.

As the pusher 21 is further pushed into the main sheath assembly 100, the stent graft 200 begins to move axially with respect to the transfer sheath 30 such that it is transferred from the transfer sheath 30 into the main sheath 105. This prevents the transfer sheath 30 from progressing too far into the valve assembly 110 and hence prevents the transfer sheath 30 becoming jammed in the valve within the valve assembly 110. The relative length of the stopper 40 and the temporary transfer sheath 30 is such that the transfer sheath 30 is held at a pre-determined position inside the valve assembly 110, so as to prevent both the possibility of graft deployment within the valve assembly 110 and the possibility of the transfer sheath 30 becoming jammed inside the valve assembly 110. The longitudinal slit 45 is provided so that the stopper 40 is easily removable when no longer required. FIG. 11A shows the stopper 40 of FIG. 7A around the transfer sheath 30 and FIG. 11B shows the stopper 40 of FIG. 7A being removed from the transfer sheath 30. The material thickness and properties of the stopper 40 are such that, even with the longitudinal split 45, it is positively located so that it is not easily dislodged accidently from its coaxial position around the transfer sheath 30.

An advantage of the arrangement described above is that its operators do not require as much training and do not need as much skill to transfer a graft 200 into a main sheath 100 during and endovascular procedure. Furthermore, the likelihood of jamming is reduced, as described above.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any art in this specification is not, and should not be taken as, an acknowledgement of any form of suggestion that such prior art forms part of the common general knowledge.

It will be appreciated by those skilled in the art that the invention is not restricted in its use to the particular application described. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. An endograft introducer assembly comprising:
   a pusher assembly comprising a guide wire catheter, a tip mounted to a proximal end of the guide wire catheter, a stent graft receiving portion distal of the tip and a pusher distal of the receiving portion;
   a transfer sheath extending distally over the stent graft receiving portion from a proximal position adjacent to the tip, the transfer sheath having a first length over the stent graft receiving portion and a distal end; and
   a stopper disposed co-axially around the transfer sheath, the stopper having a proximal end terminating in a stopper surface and a distal portion, the distal portion removably engaged with the transfer sheath so as to prevent relative axial movement between the stopper and the transfer sheath in at least one direction,
   wherein the transfer sheath comprises a return portion at its distal end that extends out of a distal opening at a distal end of the stopper, extends back over a distal portion of the transfer sheath such that the return portion is concentric with the distal portion of the transfer sheath to form a receiving space between the transfer sheath and the return portion which is configured to receive the distal portion of the stopper within the receiving space to prevent the relative axial movement.

2. The endograft introducer assembly of claim 1, wherein the stopper has a second length that is less than the first length.

3. The introducer assembly of claim 1, wherein the stopper has a longitudinal split that is configured to allow the stopper to flexibly open for lateral movement over the transfer sheath.

4. The introducer assembly of claim 1, wherein the receiving space of the return portion is configured to prevent relative axial movement between the stopper and the transfer sheath in the at least one direction.

5. The introducer assembly of claim 1, wherein the stopper has a first longitudinal stiffness and the transfer sheath has a second longitudinal stiffness less than the first longitudinal stiffness.

6. The introducer assembly of claim 1, wherein the transfer sheath is frangible so as to allow it to be removed from the pusher without the need to slide over an end of the pusher.

7. The introducer assembly of claim 1, wherein the return portion of the transfer sheath comprises a bifurcated end terminating in a pair of gripable tails.

8. An assembly comprising:
   a pusher assembly comprising a guide wire catheter, a tip mounted to a proximal end of the guide wire catheter, a stent graft receiving portion distal of the tip and a pusher distal of the receiving portion;

a transfer sheath extending distally over the stent graft receiving portion from a proximal position adjacent to the tip, the transfer sheath having a first length over the stent graft receiving portion and a stent graft mounted on the receiving portion; and a stopper disposed co-axially around the transfer sheath, the stopper having a proximal end terminating in a stopper surface and a distal portion, the distal portion removably engaged with the transfer sheath so as to prevent relative axial movement between the stopper and the transfer sheath in at least one direction, wherein the transfer sheath comprises a return portion at a distal end that extends out of a distal opening at a distal end of the stopper, extends back over a distal portion of the transfer sheath such that the return portion is concentric with the distal portion of the transfer sheath to form a receiving space between the transfer sheath and the return portion which is configured to receive the distal portion of the stopper within the receiving space to prevent the relative axial movement.

9. The assembly of claim 8, wherein the stopper has a second length that is less than the first length.

10. The assembly of claim 9, wherein the stopper has a longitudinal split that is configured to allow the stopper to flexibly open for lateral movement over the transfer sheath.

11. The assembly of claim 9, wherein the receiving space of the return portion is configured to prevent relative axial movement between the stopper and the transfer sheath in the at least one direction.

12. The assembly of claim 8, wherein the stopper has a first longitudinal stiffness and the transfer sheath has a second longitudinal stiffness less than the first longitudinal stiffness.

13. The assembly of claim 8, wherein the transfer sheath is frangible so as to allow it to be removed from the pusher without the need to slide over an end of the pusher.

14. The assembly of claim 8, wherein the return portion of the transfer sheath comprises a bifurcated end terminating in a pair of gripable tails.

15. A system comprising:
a main sheath assembly having a valve assembly, the valve assembly having a distal end face surrounding an aperture;
a pusher assembly comprising a guide wire catheter, a tip mounted to a proximal end of the guide wire catheter, a stent graft receiving portion distal of the tip and a pusher distal of the receiving portion;
a transfer sheath extending distally over the stent graft receiving portion from a proximal position adjacent to the tip, the transfer sheath having a first length over the stent graft receiving portion and a stent graft mounted on the receiving portion; and
a stopper disposed co-axially around the transfer sheath, the stopper having a proximal end terminating in a stopper surface and a distal portion, the distal portion removably engaged with the transfer sheath so as to prevent relative axial movement between the stopper and the transfer sheath in at least one direction,
wherein the transfer sheath comprises a return portion at a distal end that extends out of a distal opening at a distal end of the stopper, extends back over a distal portion of the transfer sheath such that the return portion is concentric with the distal portion of the transfer sheath to form a receiving space between the transfer sheath and the return portion which receiving space is configured to receive the distal portion of the stopper within the receiving space to prevent the relative axial movement,
wherein, in use, the pusher is configured to move axially towards the main sheath assembly so that the stopper surface abuts the distal end face of the valve assembly, and a reaction force is transmitted from the stopper surface along the stopper to the proximal end of the transfer sheath, such that the transfer sheath is held at a pre-determined position inside the valve assembly.

16. The system of claim 15, wherein the stopper has a first longitudinal stiffness and the transfer sheath has a second longitudinal stiffness less than the first longitudinal stiffness.

17. The system of claim 15, wherein the distal portion of the stopper comprises a transfer sheath receiving portion having a receiving outer diameter and wherein the stopper surface has a stopper outer diameter, the stopper outer diameter larger than the receiving outer diameter.

18. The system of claim 15, wherein the transfer sheath is frangible so as to allow it to be removed from the pusher without the need to slide over an end of the pusher.

19. The system of claim 15, wherein the return portion of the transfer sheath comprises a bifurcated end terminating in a pair of gripable tails.

* * * * *